US011607146B2

(12) United States Patent
Bremer (10) Patent No.: US 11,607,146 B2
(45) Date of Patent: Mar. 21, 2023

(54) PHOTOPLETHYSMOGRAPHY DEVICE WITH THERMAL TRAPPING AND/OR WARMING CAPABILITY AND ASSOCIATED METHODS

(71) Applicant: Welch Allyn, Inc., Skaneateles Falls, NY (US)

(72) Inventor: Edward C. Bremer, Victor, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 314 days.

(21) Appl. No.: 16/875,383

(22) Filed: May 15, 2020

(65) Prior Publication Data

US 2020/0375478 A1 Dec. 3, 2020

Related U.S. Application Data

(60) Provisional application No. 62/854,502, filed on May 30, 2019, provisional application No. 62/860,862, filed on Jun. 13, 2019.

(51) Int. Cl.
*A61B 5/0295* (2006.01)
*A61B 5/00* (2006.01)
*A61B 5/01* (2006.01)
*A61B 5/026* (2006.01)
*A61B 5/1455* (2006.01)

(52) U.S. Cl.
CPC .......... *A61B 5/0295* (2013.01); *A61B 5/0064* (2013.01); *A61B 5/0075* (2013.01); *A61B 5/0082* (2013.01); *A61B 5/01* (2013.01); *A61B 5/0261* (2013.01); *A61B 5/14552* (2013.01);
(Continued)

(58) Field of Classification Search
CPC ... A61B 5/0295; A61B 5/0064; A61B 5/0075; A61B 5/0082; A61B 5/01; A61B 5/0261; A61B 5/14552; A61B 5/683; A61B 2562/0271; A61B 2562/046; A61B 5/02055; A61B 5/1491; A61B 5/6823;
(Continued)

(56) References Cited

U.S. PATENT DOCUMENTS 4,259,963 A 4/1981 Huch
4,714,080 A 12/1987 Edgar, Jr. et al.
(Continued)

OTHER PUBLICATIONS

Y. Mendelson, PhD, and M.J. McGinn, MSc, "Skin Reflectance Pulse Oximetry: In Vivo Measurements From The Forearm and Calf", 1990, Journal of Clinical Monitoring vol. 7 No. 1 (Year: 1990).*
(Continued)

*Primary Examiner* — Eric F Winakur
*Assistant Examiner* — Abid A Mustansir
(74) *Attorney, Agent, or Firm* — Barnes & Thornburg LLP (57) ABSTRACT

A photoplethysmography (PPG) device includes an equipment module which includes a photodetector and first and second light emitting diodes (LED's) adapted to emit light of first and second wavelengths, respectively. The PPG device also includes a mask covering the patient facing extremity of the equipment module so that when the device is applied to a patient the mask is situated between the patient and the patient facing extremity. A processor is adapted to control drive current and/or operating time of the second LED to achieve an elevated localized body tissue temperature of a patient to which the PPG device is applied.

18 Claims, 6 Drawing Sheets

(52) U.S. Cl.
CPC ...... *A61B 5/683* (2013.01); *A61B 2562/0271* (2013.01)

(58) Field of Classification Search
CPC .. A61B 5/02427; A61B 5/6826; A61B 5/7214
See application file for complete search history.

(56) References Cited

U.S. PATENT DOCUMENTS

| | | | |
|---|---|---|---|
| 4,723,554 | A | 2/1988 | Oman et al. |
| 4,926,867 | A * | 5/1990 | Kanda ................ A61B 5/14552 600/334 |
| 5,007,423 | A | 4/1991 | Branstetter et al. |
| 5,158,082 | A * | 10/1992 | Jones ................ A61B 5/14552 607/113 |
| 5,560,652 | A | 10/1996 | Zoland |
| 5,766,127 | A | 6/1998 | Pologe et al. |
| 9,775,528 | B2 | 10/2017 | Vermeulen et al. |
| 9,999,397 | B2 | 6/2018 | Lee et al. |
| 10,149,628 | B2 | 12/2018 | Kim et al. |
| 10,506,944 | B2 | 12/2019 | Tognetti et al. |
| 2007/0185393 | A1 | 8/2007 | Zhou et al. |
| 2011/0054336 | A1 | 3/2011 | Jornod |
| 2012/0253156 | A1 | 10/2012 | Muhlsteff |
| 2013/0158372 | A1 * | 6/2013 | Haisley ................ A61B 5/1455 600/310 |
| 2014/0005557 | A1 | 1/2014 | Rich et al. |
| 2014/0275890 | A1 | 9/2014 | Meehan et al. |
| 2015/0190063 | A1 | 7/2015 | Zakharov et al. |
| 2016/0007929 | A1 | 1/2016 | Chuang et al. |
| 2016/0361004 | A1 | 12/2016 | Lange et al. |
| 2017/0209055 | A1 | 7/2017 | Pantelopoulos et al. |
| 2018/0028077 | A1 | 2/2018 | Wu et al. |
| 2019/0380586 | A1 * | 12/2019 | Park ..................... A61B 5/0059 |
| 2020/0229767 | A1 | 7/2020 | Eletr et al. |

OTHER PUBLICATIONS

"Photoplethysmography (PPG)," by Susha Cheriyedath, M.Sc.; last updated Feb. 27, 2019; 4 pages.

* cited by examiner

PHOTOPLETHYSMOGRAPHY DEVICE WITH THERMAL TRAPPING AND/OR WARMING CAPABILITY AND ASSOCIATED METHODS

BACKGROUND

The present disclosure claims the benefit, under 35 U.S.C. 119(e), of U.S. Provisional Application No. 62/854,502, filed May 30, 2019, and U.S. Provisional Application No. 62/860,862, filed Jun. 13, 2019, each of which is hereby incorporated by reference herein in its entirety.

BACKGROUND

The subject matter described herein relates to photoplethsymography, and particularly to a photoplethsymography (PPG) device having thermal trapping and/or warming capability and associated methods of using the device.

Photoplethysmography (PPG) is a simple, low cost, optical technique used to detect volumetric changes in biological tissue. Applications of PPG include monitoring blood oxygen saturation, blood pressure, heart rate, respiration, and arterial compliance to name just a few (*Photoplethysmography (PPG)*, https://www.news-medical.net/health/Photoplethysmography-(PPG).aspx, Susha Cheriyedath, M. Sc.).

In operation a conventional photoplethysmography device illuminates a tissue site alternately with light of first and second wavelengths, typically red (approximately 650 nm) and infrared (approximately 950 nm). Light which is not absorbed or otherwise dissipated penetrates through the tissue (transmittance PPG device) or is reflected back (reflectance PPG device). Either way the light arrives at a photodetector such as a photodiode. Taking blood oxygen saturation ($SpO_2$) as an example application, a processor estimates the $SpO_2$ value in a well-known manner as a function of the intensity of light received at the photodetector in response to the red illumination and the infrared illumination during both pulsatile and nonpulsatile phases of the patient's heart cycle.

One challenge associated with PPG devices is that the signal received at the photodetector contains both a static component and a fluctuating component (often referred to as DC and AC components). The DC component is attributable to things other than pulsatile arterial blood (e.g. flesh, bone) and is not typically of interest. The AC component is attributable to pulsating arterial blood flow and contains the information of interest. However the AC component is quite small in comparison to the DC component (on the order of 1% of the DC component). As a result, the signal may be difficult to detect and its information content may be difficult to extract.

Therefore, what is needed is a PPG device and associated methods that cause the AC component of the signal to be less difficult to detect and its information content easier to extract.

SUMMARY

An apparatus, system, or method may comprise one or more of the features recited in the appended claims and/or the following features which, alone or in any combination, may comprise patentable subject matter:

According to a first aspect of the present disclosure, a photoplethysmography (PPG) device may include an equipment module which, in turn, may include a first light emitting diode (LED) that may be adapted to emit light of a first wavelength from a patient facing extremity of the equipment module, a second LED that may be adapted to emit light of a second wavelength from the patient facing extremity of the equipment module, and a photodetector. The PPG device of the first aspect may also include a mask that may cover the patient facing extremity of the equipment module so that when the PPG device is applied to a patient the mask may be situated between the patient and the patient facing extremity.

In some embodiments of the PPG device of the first aspect, the mask may include a reflective mask. Optionally, the PPG device of the first aspect may be non-enveloping when applied to the patient. Further optionally, the photodetector of the first aspect may include a photodiode. If desired, the photodetector of the first aspect may include an array of two or more photodetectors. Alternatively or additionally, the photodetector may include a ring of photodetectors that may circumscribe the first and second LED's.

It is contemplated by the present disclosure that the PPG device of the first aspect may further include a processor that may be adapted to control a drive current and an operating time of the second LED to achieve an elevated body tissue temperature of a patient to which the PPG device may be applied. If desired, the PPG device of the first aspect may further have a temperature sensor that may be adapted to detect the elevated body tissue temperature. As such, the processor of the first aspect may be adapted to control the drive current and the operating time of the second LED to achieve and maintain the detected elevated body tissue temperature at a specified value. Optionally, the first wavelength may be from a visible portion of an electromagnetic spectrum and the second wavelength may be from an infrared portion of the electromagnetic spectrum.

According to a second aspect of the present disclosure, a photoplethysmography (PPG) device may include a first light emitting diode (LED) that may be adapted to emit light of a first wavelength, a second LED that may be adapted to emit light of a second wavelength, and a photodetector. The PPG device of the second aspect may also include a processor that may be adapted to control a drive current and/or an operating time of the second LED to achieve an elevated localized body tissue temperature of a patient to which the PPG device may be applied.

In some embodiments, the PPG device of the second aspect may further include a temperature sensor that may be adapted to detect the elevated localized body tissue temperature. If desired, the processor of the second aspect may be adapted to control the drive current and/or the operating time of the second LED to achieve and maintain the elevated localized body tissue temperature at a specified value. With regard to the second aspect, the first wavelength may be from a visible portion of an electromagnetic spectrum and the second wavelength may be from an infrared portion of the electromagnetic spectrum.

According to a third aspect of the present disclosure, a method for conducting a photoplethsymographic (PPG) procedure may include illuminating a tissue sample with radiation of a first wavelength and radiation of a second wavelength, trapping radiation in the tissue sample, detecting at least a portion of tissue-reflected first wavelength radiation and tissue-reflected second wavelength radiation, and analyzing the tissue-reflected first wavelength radiation and a detected non-reintroduced second wavelength radiation to determine a parameter of interest.

In some embodiments, the method of the third aspect may further include warming the tissue sample with radiation of the second wavelength prior to detecting the at least a portion of tissue-reflected first wavelength radiation and the tissue-reflected second wavelength radiation. Optionally, the method of the third aspect may also include warming the tissue sample with radiation of the second wavelength prior to illuminating the tissue sample with radiation of the first wavelength and radiation of the second wavelength.

According to a fourth aspect of the present disclosure, a method for conducting a photoplethsymographic (PPG) procedure may include warming a tissue sample with radiation of a second wavelength, illuminating the tissue sample with radiation of a first wavelength and radiation of the second wavelength, detecting tissue-reflected first wavelength radiation and tissue-reflected second wavelength radiation, and analyzing the tissue-reflected first wavelength radiation and the tissue-reflected second wavelength radiation to determine a parameter of interest.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The foregoing and other features of the various embodiments of the PPG device described herein will become more apparent from the following detailed description and the accompanying drawings in which.

DETAILED DESCRIPTION

The present invention may comprise one or more of the features recited in the appended claims and/or one or more of the following features or combinations thereof.

In this specification and drawings, features similar to or the same as features already described may be identified by reference characters or numerals which are the same as or similar to those previously used. Similar elements may be identified by a common reference character or numeral, with suffixes being used to refer to specific occurrences of the element.

Figure 1:
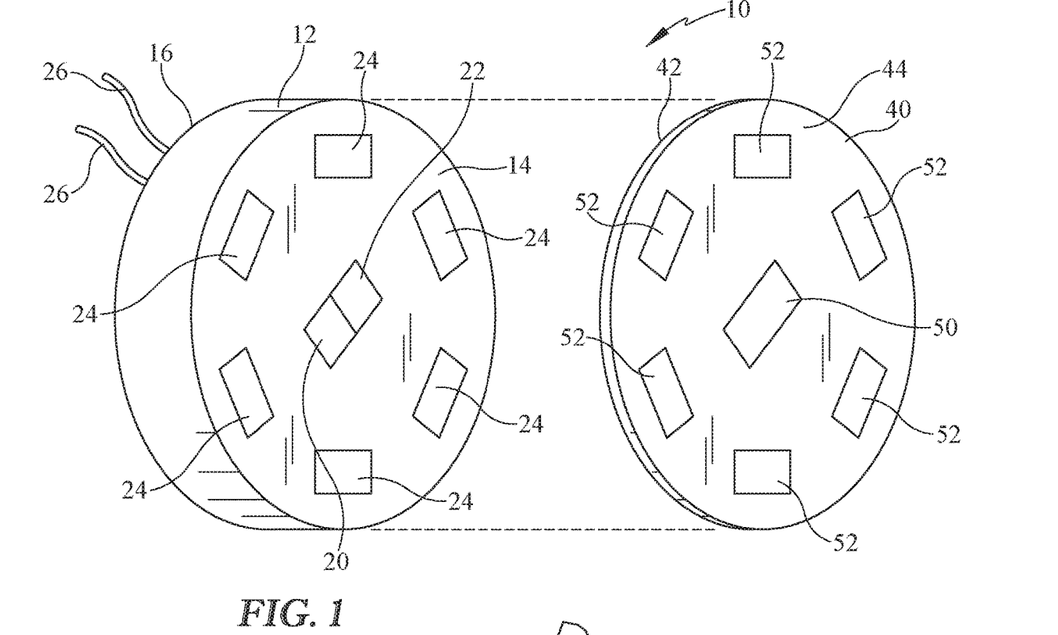
FIG. 1 is a perspective, schematic, exploded view of a PPG device including a mask and an equipment module having two light emitting diodes (LED's) and six photodetectors.
Figure 2:
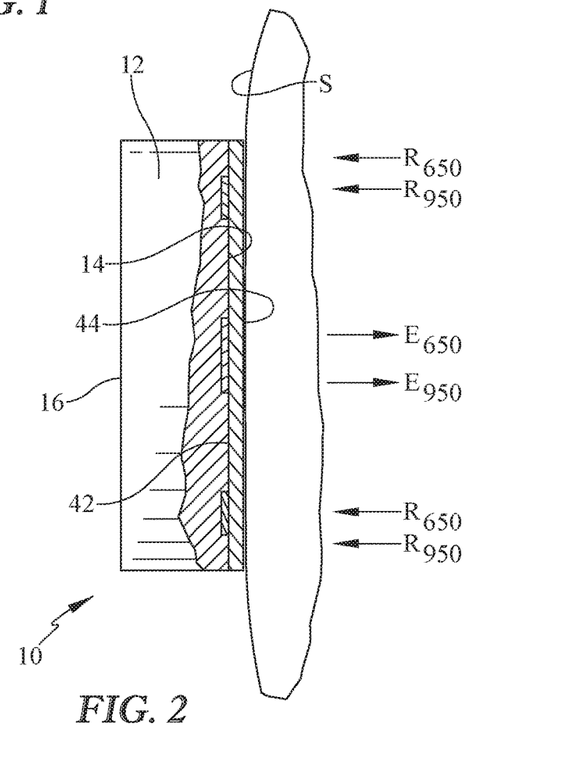
FIG. 2 is a side elevation view of the PPG device of FIG. 1 with the mask covering the patient facing side of the equipment module and showing the PPG device applied to a patient represented by the patient's skin S.

Referring to FIG. 1, a photoplethysmography (PPG) device 10 includes an equipment module 12. The equipment module 12 has a patient facing side or extremity 14 and an opposite side or extremity 16. When in use, the PPG device 10 is applied to the patient, for example by being secured to the patient, with the patient facing extremity 14 facing the patient and the opposite extremity 16 facing away from the patient. In FIG. 2 the patient is represented by a patch of skin S.

The equipment module 12 includes a first light emitting diode (LED) 20 adapted to emit light of a first wavelength $\lambda_1$ from the patient facing extremity 14 of the equipment module 12. In one embodiment the first wavelength is from the visible portion of the electromagnetic spectrum, for example about 650 nm which corresponds to visible red light. The equipment module 12 also includes a second light emitting diode 22 adapted to emit light of a second wavelength $\lambda_2$ from the patient facing extremity 14 of the equipment module 12. The second wavelength is from the infrared portion of the electromagnetic spectrum, for example about 950 nm. As is evident from the foregoing, the word "light," as used in this specification, is not limited to emissions in the visible portion of the electromagnetic spectrum.

The PPG device 10 of FIG. 1 also includes a driver, not illustrated but similar to drivers 60, 62 discussed below, for driving the LED's 20, 22.

The equipment module 12 also includes a photodetector 24 such as a photodiode. Photodiodes are used as the example of the photodetector in the balance of this specification. The illustrated embodiment includes an array of six photodiodes 24 arranged in a ring that circumscribes the first and second LED's 20, 22.

Wires 26 extend from opposite side 16 of the PPG device 10 to connect the device 10 to an electrical power source and, if necessary, to provide an information or data communication pathway. In other embodiments the device 10 may be powered by an on-board battery and/or the communication may be by wireless communication.

The PPG 10 device also includes a mask 40 having a module facing side 42 and a patient facing side 44. In one embodiment the mask 40 includes an aluminum foil layer that reflects radiation back into the tissue. Such a reflective mask 40 may reflect radiation across a broad spectrum of wavelengths or may be tailored to reflect radiation of only a selected wavelength band. In another embodiment, the mask 40 is an insulating mask which is not necessarily reflective.

Mask 40 includes a center window 50 and a set of six peripheral windows 52. As seen best in FIG. 2, the mask 40 covers the patient facing extremity 14 of the equipment module 12 so that when the PPG device 10 is applied to a patient, the mask 40 is situated between the patient and the patient facing extremity 14 of the equipment module 12. In addition, center window 50 registers with LED's 20, 22, and each peripheral window 52 registers with a respective one of the photodiodes 24.

Window 50 is transparent to the wavelengths of light emitted by LED's 20, 22. Taking 650 nm and 950 nm as an example, in one embodiment, the entire center window 50 is transparent to at least 650 nm and 950 nm light. In another embodiment, center window 50 has a first segment which overlies first LED 20 and is transparent to 650 nm light, and a second segment which overlies second LED 22 and is transparent to 950 nm light. Yet another embodiment includes two separate windows, one overlying the 650 nm first LED and transparent to 650 nm light, and the other overlying the 950 nm first LED and transparent to 950 nm light. Window or windows 50 may be openings, or may be a material having the requisite transparency.

In order for the photodiodes 24 to receive light reflected from the patient's tissue at both the first and second wavelengths, peripheral windows 52 are transparent to those wavelengths. Windows 52 may be openings, or may be a material having the requisite transparency.

Figure 3:
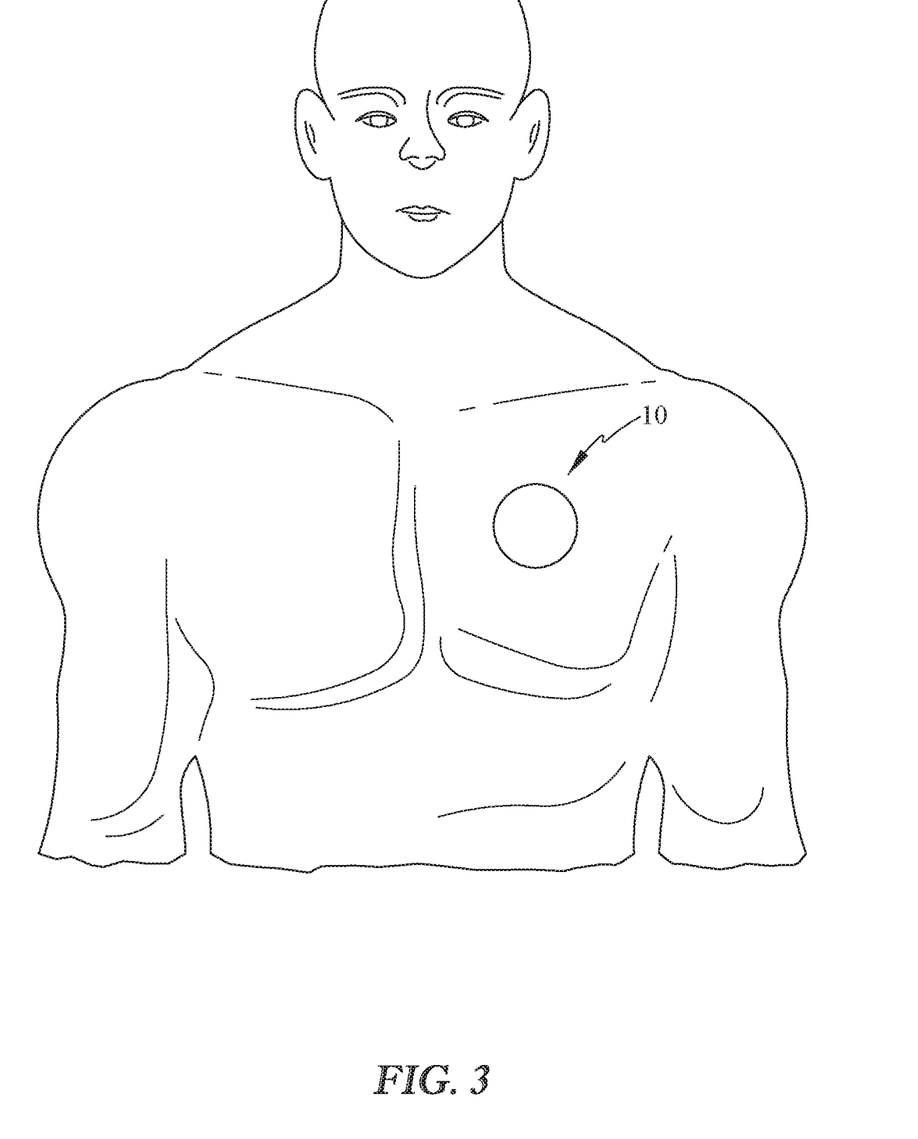
FIG. 3 is a view showing the PPG device applied to a patient.
Figure 4:
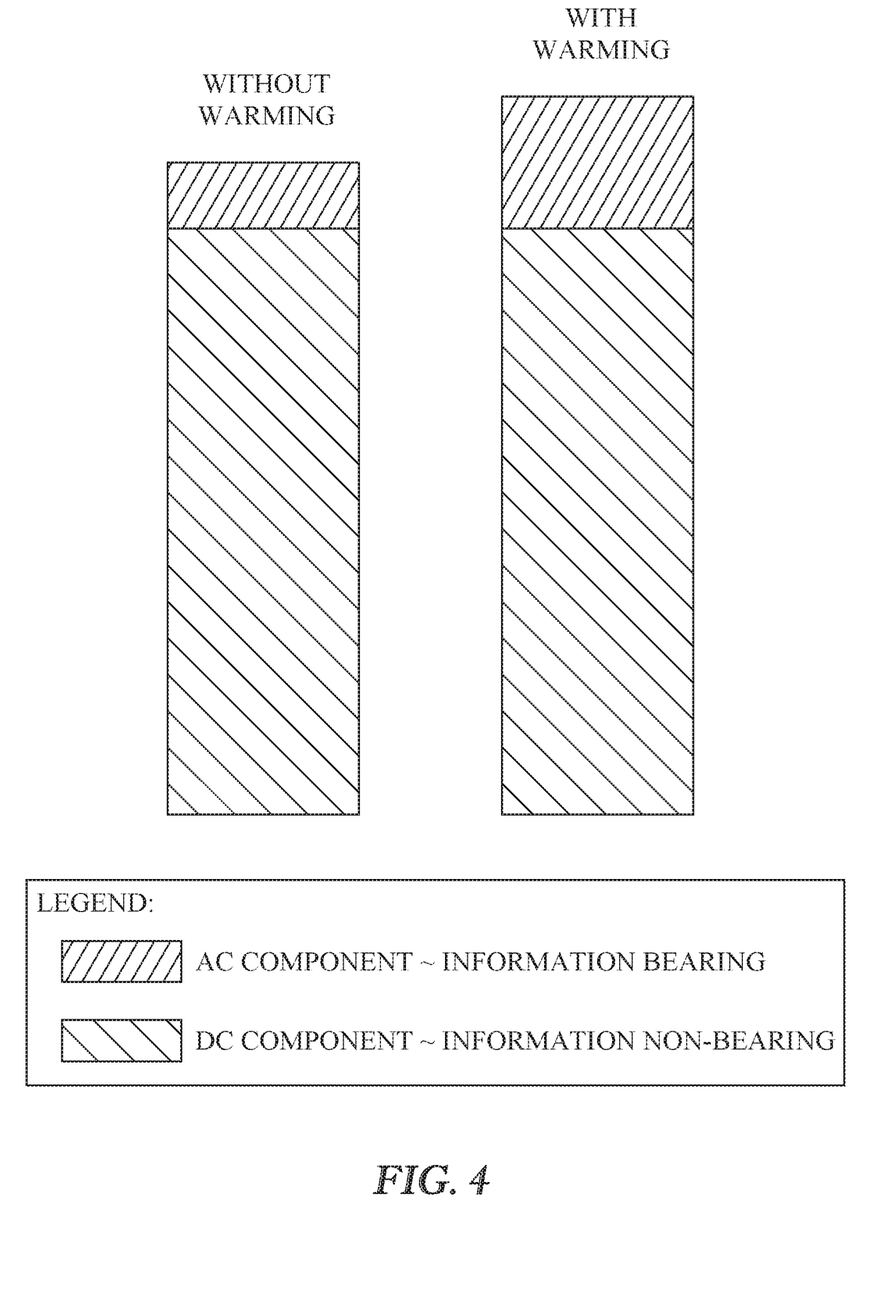
FIG. 4 is a set of bar graphs schematically illustrating the effect of the PPG device embodiments described herein on the signal received at the photodetectors.

In operation, the device 10 is applied to the patient as seen best in FIGS. 2 and 3. FIG. 3 shows the PPG device 10 applied to the patient's chest, however it may be applied elsewhere. Continuing to use the example of 650 and 950 nm light, the light emissions from first and second LED's enter the patient's tissue (arrows $E_{650}$, $E_{950}$). Light reflected back from the patient's tissue, $R_{650}$, $R_{950}$, arrives at the photodiodes 24 due to the transparency of peripheral windows 52 to the 650 and 950 wavelengths. The tissue-reflected radiation that does not pass through windows 52 (or through window 50) is trapped in the tissue by the mask 40. The trapped radiation, whether or not introduced by the 650 nm and 950 nm light sources, causes warming of the tissue above and beyond any warming that might occur if the mask 40 were not present. The pulsating arterial blood flow increases in response to the warmth. The tissue other than the pulsating arterial blood (e.g. flesh, bone) is largely or entirely unaffected by the warmth. Referring additionally to FIG. 4, the information bearing AC portion of the "warm" signal received at the photodetectors 24 is therefore amplified in comparison to the "cold" AC signal that would be obtained without the warming attributable to the mask 40. The "warm" AC signal is therefore larger than the "cold" AC signal, both in absolute terms and in proportion to the DC component of the signal. As a result the "warm" AC signal is easier to detect, and its information content is easier to extract than is the case with the "cold" AC signal.

Figure 5:
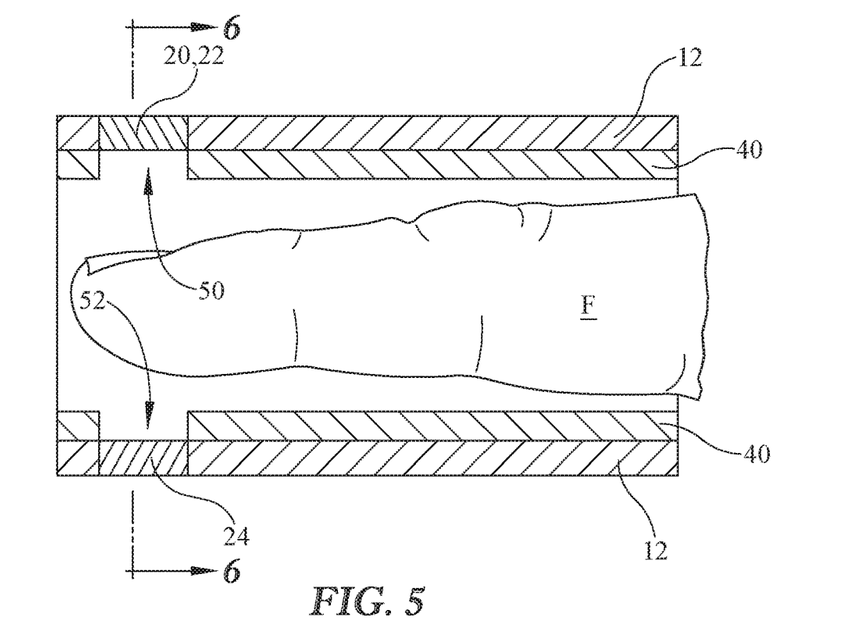
FIGS. 5 and 6 are a cross sectional side elevation view and an end elevation view of an enveloping embodiment of the PPG device.
Figure 6:
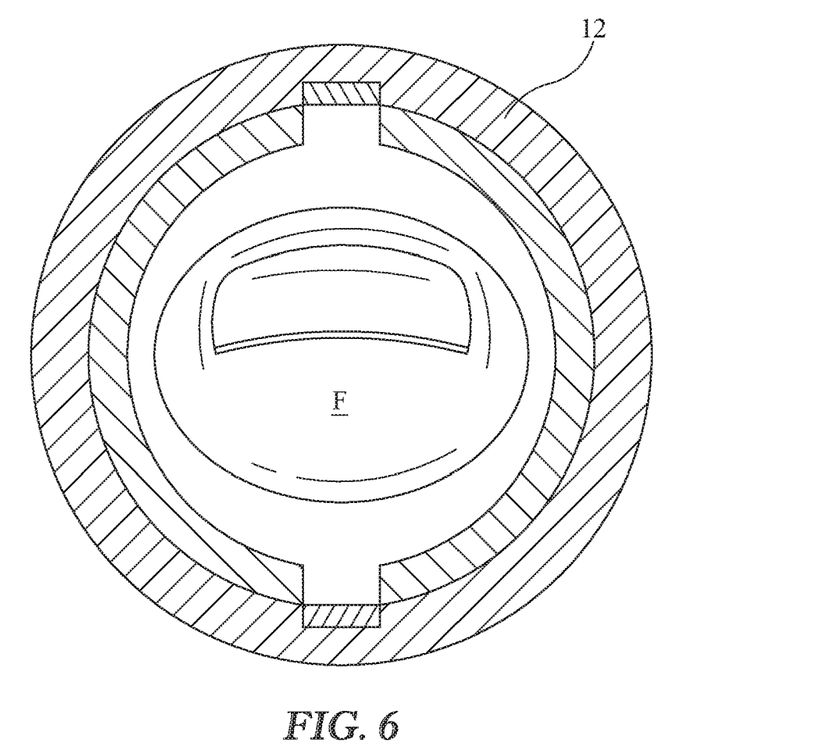

As seen in FIGS. 2 and 3, the PPG device 10, as applied to a patient, is non-enveloping. In other words, the device 10 does not envelope a portion of the patient's anatomy. FIGS. 5 and 6 show an alternative in which the PPG device envelopes or partially envelops a patient's finger F. The space between the patient and the PPG device is exaggerated to preserve the clarity of the illustration. Because the LED's 20, 22 and photodetector 24 are on opposite sides of the patient's finger, the device of FIGS. 5 and 6 is a transmittance PPG device. The principles already described nevertheless apply. That is, mask 40 on module 12 traps radiation in the patient's finger F causing the tissue warming and beneficial effect on the AC component of the signal received at the photodetector 24 as already described.

A method for conducting a photoplethsymographic (PPG) procedure in accordance with the embodiments described above includes illuminating a tissue sample with radiation of a first wavelength and radiation of a second wavelength, and trapping radiation in the tissue sample. The method includes detecting at least a portion of tissue-reflected first wavelength radiation and tissue-reflected second wavelength radiation (i.e. the radiation that was not trapped in the tissue). The method also includes analyzing the detected first wavelength radiation and the detected second wavelength radiation to determine a parameter of interest. Such parameter of interest may include blood oxygen saturation, to name just one of many that will occur to those skilled in the art.

Figure 7:
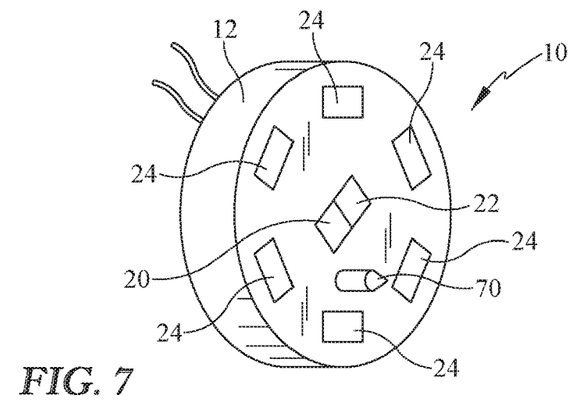
FIGS. 7 and 8 are a schematic and a perspective view showing a PPG device having light emitting diodes, LED drivers, a photodetector, a temperature sensor, and a processor adapted to regulate drive current and/or operating time of one of the LED's.
Figure 8:
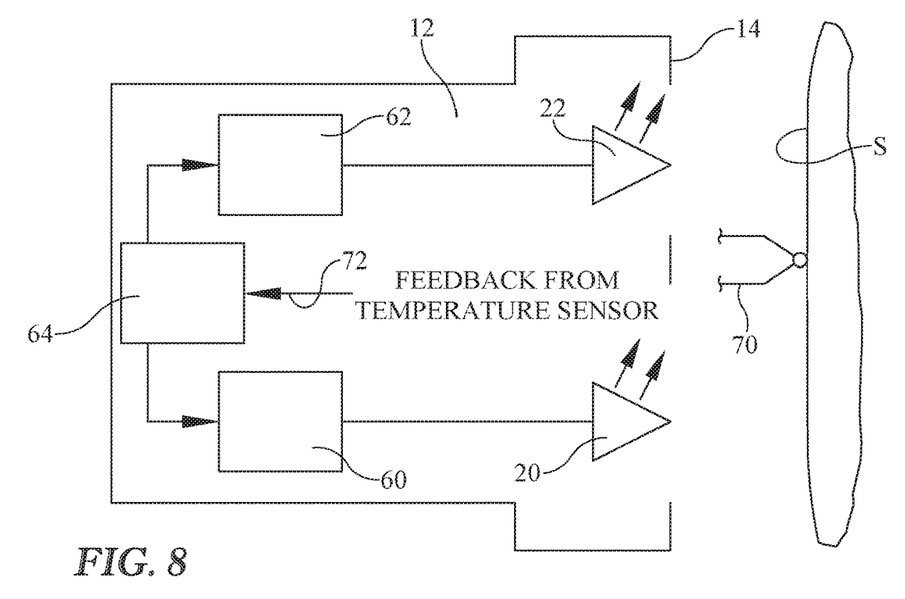

Referring to FIGS. 7 and 8 a PPG device 10 includes a first LED 20 adapted to emit light of a first wavelength $\lambda_1$ (e.g. a visible wavelength such as 650 nm), a second LED 22 adapted to emit light of a second wavelength $\lambda_2$ (e.g. an infrared wavelength such as 950 nm) and a photodetector 24. The foregoing description of these components in connection with the PPG device 10 shown in FIGS. 1, 2, 5 and 6 also applies to the device 10 of FIGS. 7 and 8. The PPG device 10 also includes first and second LED drivers 60, 62 and a processor 64. A patient is represented by a patch of skin S. The space between the patient and the PPG device 10 is exaggerated to preserve the clarity of the illustration.

Processor 64 is adapted to control the drive current output from second LED driver 62 and/or the operating time of the second LED 22 in order to achieve an elevated localized body tissue temperature of the patient to which the PPG device 10 is applied. Elevated temperature means a temperature higher than that which would result if the drive current and/or LED operating time were not controlled in a way intended to achieve a tissue temperature high enough to boost the AC portion of the signal received at the photodetector 24 as seen in FIG. 4. For example the processor 64 may cause the driver 62 to supply more drive current to the second LED 22 than would be the case if the thermal effect on the tissue and the accompanying beneficial effect on the AC portion of the signal (FIG. 4) were not sought. Or, the processor 64 may cause the second LED 22 to illuminate the tissue for longer time intervals than would be necessary if the thermal effect on the tissue and the accompanying beneficial effect on the AC portion of the signal (FIG. 4) were not sought. Or, the processor 64 may command a combination of increased drive current and increased LED operating time.

The PPG may also include a temperature sensor adapted to detect the body tissue temperature. In FIGS. 7 and 8 the temperature sensor is illustrated as a thermocouple 70. Feedback 72 from the temperature sensor 70 is used to control drive current and/or operating time of the second LED 22 to achieve and maintain the detected body tissue temperature at a specified value. One temperature believed to be satisfactory is about 40° C.

Figure 9:
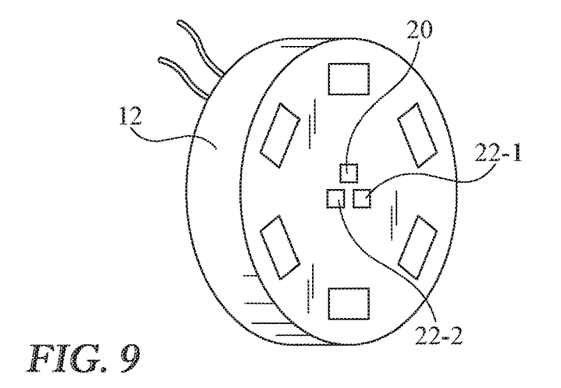
FIG. 9 is a view similar to FIG. 7 showing a PPG device with three LED's, one of which is dedicated to warming the patient's skin.

FIG. 9 shows an embodiment of the PPG device of FIGS. 7 and 8 having a first LED 20 adapted to emit light of a first wavelength $\lambda_1$ (e.g. a visible wavelength such as 650 nm). The PPG device also includes an array of one or more second LED's 22-1, 22-2 all adapted to emit light of a second wavelength $\lambda_2$ (e.g. an infrared wavelength such as 950 nm). The second LED's 22-1, 22-2 provide illumination at a second (e.g. infrared) wavelength, just as in a conventional PPG device. The second LED's 22-1, 22-2 also help to achieve the elevated body tissue temperature. In one embodiment, several second LED's are provided in order to achieve the desired tissue warming effect and the attendant beneficial effect on the AC portion of the signal as shown in FIG. 4. In addition, the embodiment of FIG. 9 may include the temperature sensor of FIGS. 7 and 8 for the purposes already described.

A method for conducting a photoplethsymographic (PPG) procedure in accordance with the embodiments described above includes warming a tissue sample with radiation of a second wavelength and illuminating the tissue sample with radiation of a first wavelength and radiation of the second wavelength. The method also includes detecting tissue-reflected first wavelength radiation and tissue-reflected second wavelength radiation. The method also includes analyzing the detected first wavelength radiation and the detected second wavelength radiation to determine a parameter of interest.

Figure 10:
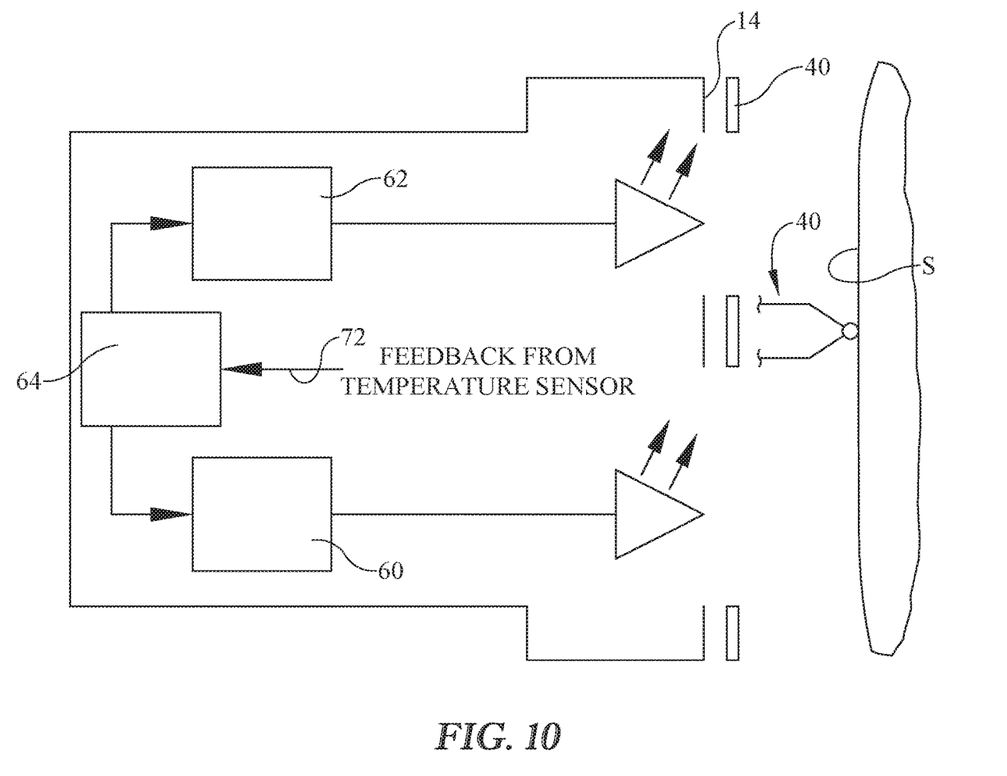
FIGS. 10 and 11 are views similar to those of FIGS. 7 and 8 showing an embodiment which includes the mask of the embodiment of FIGS. 1, 2, 5 and 6 and the temperature sensor and processor of FIGS. 7 and 8.
Figure 11:
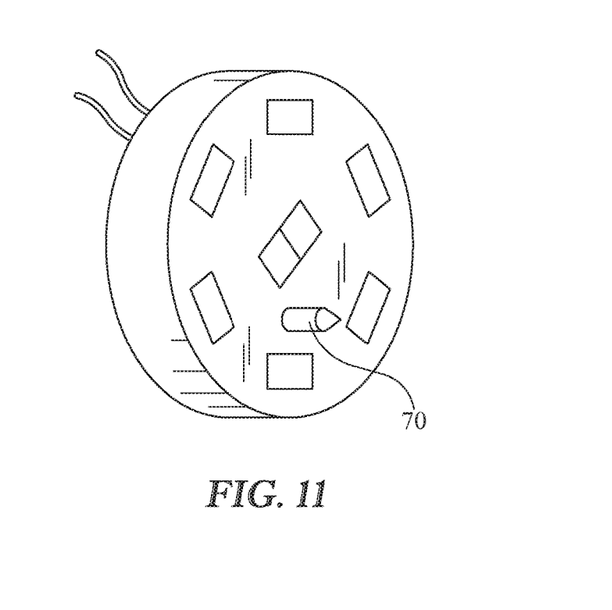

FIGS. 10 and 11 show a PPG device which includes both a mask 40 as in FIGS. 1, 2, 5 and 6, and a processor 64 adapted to control drive current and operating time of the second LED to achieve an elevated localized body tissue temperature of a patient to which the PPG device is applied as in FIGS. 7 and 9. The embodiment of FIGS. 10 and 11 combines the features and operational benefits of the embodiments of FIGS. 1, 2, 5 and 6 with the features and operational benefits of the embodiment of FIGS. 7 and 9.

A method for conducting a photoplethsymographic (PPG) procedure in accordance with the combined embodiments described above includes warming a tissue sample with radiation of a second wavelength and trapping heat energy in the tissue sample. The method also includes illuminating the tissue sample with radiation of a first wavelength and radiation of the second wavelength. The method also includes detecting at least a portion of tissue-reflected first wavelength radiation and at least a portion of tissue-reflected second wavelength radiation (i.e. the tissue reflected first and second wavelength radiation that was not trapped in the tissue). The method also includes analyzing the detected first wavelength radiation and the detected second wavelength radiation to determine a parameter of interest.

Although this disclosure refers to specific embodiments, it will be understood by those skilled in the art that various changes in form and detail may be made without departing from the subject matter set forth in the accompanying claims.

The invention claimed is:

1. A photoplethysmography (PPG) device comprising:
an equipment module which includes:
a first light emitting diode (LED) adapted to emit light of a first wavelength from a patient facing extremity of the equipment module;
a second LED adapted to emit light of a second wavelength from the patient facing extremity of the equipment module; and
a photodetector; and
a mask covering the patient facing extremity of the equipment module so that when the PPG device is applied to a patient the mask is situated between the patient and the patient facing extremity, wherein the mask comprises a plate-like member having a first window that registers with both the first LED and the second LED and having a second window spaced from the first window that registers with the photodetector, wherein the plate-like member comprises a unitary aluminum foil layer through which the first and second windows extend.

2. The PPG device of claim 1, wherein the mask comprises a reflective mask.

3. The PPG device of claim 1, wherein the PPG device is non-enveloping when applied to the patient.

4. The PPG device of claim 1, wherein the photodetector comprises a photodiode.

5. The PPG device of claim 1, wherein the photodetector comprises an array of two or more photodetectors.

6. The PPG device of claim 5, wherein the photodetector comprises a ring of photodetectors circumscribing the first and second LED's.

7. The PPG device of claim 1, further comprising a processor adapted to control a drive current and an operating time of the second LED to achieve an elevated body tissue temperature of a patient to which the PPG device is applied.

8. The PPG device of claim 7, further comprising a temperature sensor adapted to detect the elevated body tissue temperature.

9. The PPG device of claim 8, wherein the processor is adapted to control the drive current and the operating time of the second LED to achieve and maintain the detected elevated body tissue temperature at a specified value.

10. The PPG device of claim 7, wherein the first wavelength is from a visible portion of an electromagnetic spectrum and the second wavelength is from an infrared portion of the electromagnetic spectrum.

11. A photoplethysmography (PPG) device comprising:
a first light emitting diode (LED) adapted to emit light of a first wavelength;
a second LED adapted to emit light of a second wavelength;
a photodetector;
a processor adapted to control a drive current and/or an operating time of the second LED to achieve an elevated localized body tissue temperature of a patient to which the PPG device is applied, and
a mask, wherein the mask comprises a plate-like member having a first window that registers with both the first LED and the second LED without receiving the first and second LED's therein and having a second window spaced from the first window that registers with the photodetector without receiving the photodetector therein, wherein the plate-like member comprises a unitary aluminum foil layer through which the first and second windows extend.

12. The PPG device of claim 11, further comprising a temperature sensor adapted to detect the elevated localized body tissue temperature.

13. The PPG device of claim 12, wherein the processor is adapted to control the drive current and/or the operating time of the second LED to achieve and maintain the elevated localized body tissue temperature at a specified value.

14. The PPG device of claim 11, wherein the first wavelength is from a visible portion of an electromagnetic spectrum and the second wavelength is from an infrared portion of the electromagnetic spectrum.

15. A method for conducting a photoplethsymographic (PPG) procedure on a person, the method comprising:
illuminating, through a first window of a plate-like mask, a tissue sample of the person with radiation of a first wavelength emitted from a first light emitting diode (LED) and radiation of a second wavelength emitted from a second LED;
trapping radiation in the tissue sample;
detecting, through a second window of the plate-like mask, at least a portion of tissue-reflected first wavelength radiation and tissue-reflected second wavelength radiation, wherein the second window is spaced from the first window, wherein the plate-like mask comprises a unitary aluminum foil layer, wherein the first and second windows comprise respective openings extending through the unitary aluminum foil layer, and wherein the mask further comprises a transparent material that fills the openings; and
analyzing the tissue-reflected first wavelength radiation and a detected non-reintroduced second wavelength radiation to determine a parameter of interest, wherein the parameter of interest includes one or more of the following: blood oxygen saturation, blood pressure, heart rate, respiration, and arterial compliance of the person.

16. The method of claim 15, further comprising warming the tissue sample with radiation of the second wavelength prior to detecting the at least a portion of tissue-reflected first wavelength radiation and the tissue-reflected second wavelength radiation.

17. The method of claim 15, further comprising warming the tissue sample with radiation of the second wavelength prior to illuminating the tissue sample with radiation of the first wavelength and radiation of the second wavelength.

18. A method for conducting a photoplethsymographic (PPG) procedure on a person, the method comprising:
   warming a tissue sample of the person with radiation of a second wavelength emitted from a second light emitting diode (LED);
   illuminating the tissue sample with radiation of a first wavelength emitted from a first LED and radiation of the second wavelength emitted from the second LED, wherein the first LED and the second LED are in registry with a first window of a plate-like mask;
   detecting, through a second window of the plate-like mask, tissue-reflected first wavelength radiation and tissue-reflected second wavelength radiation, wherein the second window is spaced from the first window, wherein the plate-like mask comprises a unitary aluminum foil layer through which the first and second windows extend, wherein the first and second windows comprise respective openings extending through the unitary aluminum foil layer, and wherein the mask further comprises a transparent material that fills the openings; and
   analyzing the tissue-reflected first wavelength radiation and the tissue-reflected second wavelength radiation to determine a parameter of interest, wherein the parameter of interest includes one or more of the following: blood oxygen saturation, blood pressure, heart rate, respiration, and arterial compliance of the person.

* * * * *